United States Patent
Muralimanohar et al.

(10) Patent No.: US 8,938,589 B2
(45) Date of Patent: Jan. 20, 2015

(54) INTERFACE METHODS AND APPARATUS FOR MEMORY DEVICES USING ARBITRATION

(75) Inventors: Naveen Muralimanohar, Santa Clara, CA (US); Norman Paul Jouppi, Palo Alto, CA (US)

(73) Assignee: Hewlett-Packard Development Company, L. P., Houston, TX (US)

( * ) Notice: Subject to any disclaimer, the term of this patent is extended or adjusted under 35 U.S.C. 154(b) by 321 days.

(21) Appl. No.: 13/386,396

(22) PCT Filed: Jan. 27, 2011

(86) PCT No.: PCT/US2011/022762
§ 371 (c)(1),
(2), (4) Date: Jan. 20, 2012

(87) PCT Pub. No.: WO2011/094436
PCT Pub. Date: Aug. 4, 2011

(65) Prior Publication Data
US 2012/0151159 A1 Jun. 14, 2012

Related U.S. Application Data

(60) Provisional application No. 61/299,128, filed on Jan. 28, 2010.

(51) Int. Cl.
*G06F 12/00* (2006.01)
*G06F 3/00* (2006.01)
(Continued)

(52) U.S. Cl.
CPC ............... *A01N 65/36* (2013.01); *A01N 65/00* (2013.01); *A01N 65/08* (2013.01)
USPC ........... 711/152; 711/156; 711/163; 711/167; 710/17; 710/18; 710/19; 710/39

(58) Field of Classification Search
CPC ....... G06F 3/0601; G06F 3/062; G06F 3/061; G06F 3/0611; G06F 3/0613; G06F 3/0625; G06F 3/0614; G06F 3/0616; G06F 3/0617; G06F 13/14; G06F 14/42; G06F 13/4234; G06F 11/30; G06F 11/3034
USPC ........ 711/152, 156, 163, 167; 710/17, 18, 19, 710/58, 59
See application file for complete search history.

(56) References Cited

U.S. PATENT DOCUMENTS 5,606,717 A 2/1997 Farmwald et al.
6,052,772 A 4/2000 Kark et al.
(Continued)

FOREIGN PATENT DOCUMENTS

EP 0718770 A1 6/1996
JP 2010146145 7/2010
(Continued)

OTHER PUBLICATIONS

EP Search Report~Application No: 11737662.4 (PCT/US2011/022762) dated May 17, 2013~sent May 31, 2013~6 pages.
(Continued)

*Primary Examiner* — John Lane
(74) *Attorney, Agent, or Firm* — Hanley Flight & Zimmerman; Felipe Hernandez

(57) ABSTRACT

A disclosed example apparatus includes an interface (702, 726) to receive a request to access a memory (602*a*) of a memory module (600) and a data store status monitor (730) to determine a status of the memory. The example apparatus also includes a message output subsystem (732) to, when the memory is busy, respond to the request with a negative acknowledgement indicating that the request to access the memory is not grantable.

18 Claims, 8 Drawing Sheets

(51) Int. Cl.
*A01N 65/36* (2009.01)
*A01N 65/00* (2009.01)
*A01N 65/08* (2009.01)

(56) References Cited

U.S. PATENT DOCUMENTS

| | | | |
|---|---|---|---|
| 6,061,290 | A | 5/2000 | Shirley |
| 6,360,285 | B1 | 3/2002 | Fenwick et al. |
| 6,523,098 | B1 | 2/2003 | Anderson |
| 6,768,692 | B2 | 7/2004 | Luk et al. |
| 7,020,741 | B1 | 3/2006 | Tischler |
| 7,409,491 | B2 | 8/2008 | Doblar et al. |
| 7,533,212 | B1 | 5/2009 | Doblar et al. |
| 7,872,892 | B2 | 1/2011 | MacWilliams et al. |
| 8,230,120 | B2 * | 7/2012 | Ajanovic et al. ........... 710/5 |
| 8,407,445 | B1 * | 3/2013 | Pathak et al. ........... 711/170 |
| 8,538,998 | B2 * | 9/2013 | Barrow ........... 707/802 |
| 2005/0216678 | A1 | 9/2005 | Jeddeloh |
| 2008/0005479 | A1 | 1/2008 | Tremaine |
| 2008/0276048 | A1 | 11/2008 | Booth et al. |
| 2009/0013211 | A1 | 1/2009 | Vogt et al. |
| 2009/0097851 | A1 | 4/2009 | Tan et al. |
| 2009/0204629 | A1 * | 8/2009 | Barrow ........... 707/102 |
| 2009/0254689 | A1 | 10/2009 | Karamcheti et al. |
| 2009/0282182 | A1 | 11/2009 | Jeddeloh |
| 2010/0080076 | A1 | 4/2010 | Bains et al. |
| 2010/0191914 | A1 * | 7/2010 | Cantin ........... 711/122 |
| 2010/0250856 | A1 * | 9/2010 | Owen et al. ........... 711/128 |
| 2010/0299667 | A1 * | 11/2010 | Ahmad et al. ........... 718/1 |
| 2011/0238882 | A1 * | 9/2011 | Ajanovic et al. ........... 710/305 |

FOREIGN PATENT DOCUMENTS

| | | |
|---|---|---|
| WO | 2011094436 | 8/2011 |
| WO | 2011094437 | 8/2011 |

OTHER PUBLICATIONS

International Search Report, PCT/US2011/022762, Sep. 1, 2011, 9 pages.

J. Ahn et al., "Multicore DIMM: an Energy Efficient Memory Module with Independently Controlled DRAMs", IEEE Computer Architecture Letters, vol. 7(1), 4 pages, 2008.

E. Cooper-Balis et al., "Fine-Grained Activation for Power Reduction in DRAM", IEEE: Micro, 14 pages, May 2010.

K. Sudan et al., "Micro-Pages Increasing DRAM Efficiency with Locality-Aware Data Placement", Proc. ASPLOS, pp. 219-230, Mar. 13, 2010.

D. H. Yoon et al., "Adaptive Granularity Memory Systems: A Tradeoff between Storage Efficiency and Throughput", Proc. ISCA, 12 pages, Jun. 4, 2011.

H. Zheng et al., "Mini-Rank: Adaptive DRAM Architecture or Improving Memory Power Efficiency", Proceedings of MICRO, pp. 210-221, 2008.

Wikipedia, "Synchronous Dynamic Random Access Memory," retrieved from http://en.wikipedia.org/wiki/Synchronous_dynamic_random_access_memory on Feb. 10, 2011, 12 pages.

T. J. Dell, "A Whitepaper on the Benefits of Chipkill-Correct ECC for PC Server Main Memory," Technical report, IBM Microelectronics Division, 24 Pages, Nov. 19, 1997.

D. Locklear, "Chipkill Correct Memory Architecture," Technical Report, Dell, 4 pages, Aug. 2000.

Wikipedia, "Memristor," retrieved from http://en.wikipedia.org/windex.php?title=Memristor&oldid=328659258 on Dec. 4, 2009, 18 pages.

Bryan Gardiner, "Scientists Create First Memristor: Missing Fourth Electronic Circuit Element," retrieved from http://www.wired.com/gadgetlab/2008/04/scientists-prov/ on Dec. 4, 2009, 3 pages.

Michael Brown."White Paper: The Memristor," retrieved from http//www.maximumpc.com/print/5814 on Dec. 4, 2009, 4 pages.

Vantrease. et al., "Light Speed Arbitration and Flow Control for Nanophotonic Interconnects," MICRO, Dec. 12, 2009, New York, NY (12 pages).

"Heard at Hot Interconnects: Multicore SoCs may require optical interconnect," Reed Business Information, Aug. 27, 2008 [retrieved from http://www.edn.com/electronics-blogs/practical-chip-design/4309449/Heard-at-Hot-Interconnects-Muiticore-SoCs-may-require-optical-interconnect, on Dec. 11, 2009](2 pages).

Udipi, et al. "Rethinking DRAM Design andOranizationor Energy-Constrained Multi-Cores," ISCA, Saint-Malo, France, Jun. 19-23, 2010 (12 pages).

Ahn, et al., "Future Scaling of Processor-Memory Interfaces," SC09 Nov. 14-20, 2009 (12 pages).

Wikipedia., "Dynamic Random Access Memory," retrieved from http://en.wiikipedia.org/wiki/Dynamic_random-access_memory on Feb. 10, 2011 (15 pages).

* cited by examiner

READ/WRITE BUS PACKET

HINT BUS PACKET

RESPONSE BUS PACKET

INTERFACE METHODS AND APPARATUS FOR MEMORY DEVICES USING ARBITRATION

RELATED APPLICATIONS

This is an International Patent Cooperation Treaty patent application that claims the benefit of U.S. Provisional Patent Application No. 61/299,158, filed on Jan. 28, 2010, which is hereby incorporated herein by reference in its entirety.

BACKGROUND

Traditionally, memories such as dynamic random access memories (DRAMs) have been designed to operate strictly in accordance with commands from memory controllers such that known DRAM devices execute received commands in a passive manner without deviation. Thus, DRAM devices have traditionally had little to no independent logic and, thus, have exhibited a low-degree of autonomy. For example, synchronous DRAM (SDRAM) devices operate in accordance with a clock signal such that communications (e.g., read, write, data communications) must be received, processed, and output in accordance with strict timing guidelines associated with the clock signal.

Traditional DRAM physical interfaces include separate address and data lines and separate command lines to accommodate communications between a memory controller and memory devices. To perform read or write operations, a memory controller first sends part of an address called a row address, which a DRAM uses to identify a bank and read a corresponding row. The memory controller then sends a column address to identify a particular cache line in an open row. In addition, the memory controller sends separate control signals to differentiate between row addresses and column addresses. Thus, a DRAM relies on numerous signals and communications from a memory controller for a significant amount of its operations.

DETAILED DESCRIPTION

Figure 1:
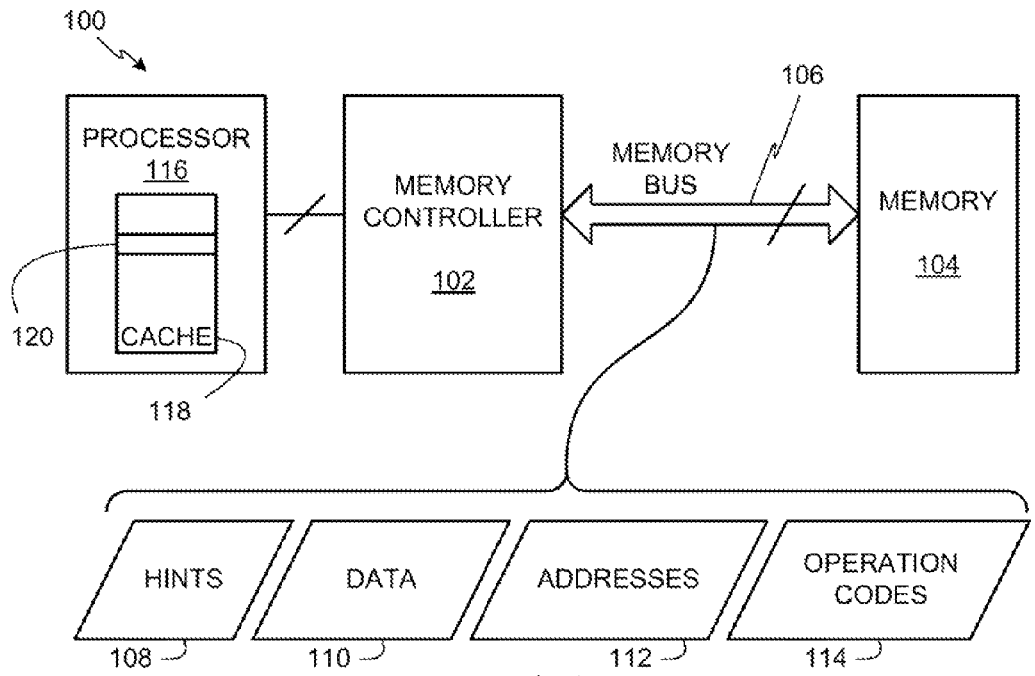
FIG. 1 depicts a block diagram of an interface configuration between a memory controller and a memory.

Example methods, apparatus, and articles of manufacture disclosed herein can be used to facilitate greater scalability than can be achieved using traditional DRAM interface designs without increasing (or without significantly increasing) processor overhead. In addition to greater scalability, example methods, apparatus, and articles of manufacture disclosed herein can be used to interface with memory devices to achieve higher bandwidth memory accesses and more power-efficient and time-efficient memory accesses. Example methods, apparatus, and articles of manufacture are disclosed in connection with dynamic random access memory (DRAM) architectures, but may be implemented in connection with other types of memories including memristor memory devices, phase-change RAM (PCRAM) devices, static RAM (SRAM) devices, Ferroelectric RAM (FRAM) devices, etc.

Traditionally, DRAM devices have been designed to operate strictly in accordance with commands from memory controllers such that known DRAM devices execute received commands in a passive manner without deviation. Thus, DRAM devices have traditionally had little to no independent logic and, thus, have exhibited a low-degree of autonomy. For example, synchronous DRAM (SDRAM) devices operate in accordance with a clock signal such that communications (e.g., read, write, data communications) must be received, processed, and output in accordance with strict timing guidelines associated with the clock signal. In addition, physical interfaces of traditional DRAM devices pose limitations for expanding capacity and achieving higher data rate communications. That is, traditional DRAM physical interfaces include separate address and data lines and separate command lines that are not easily expandable. In addition, traditional DRAM physical interfaces accommodate communications between a memory controller and memory devices but not memory device-to-memory device communications.

While the simplicity of traditional DRAM interface designs enable simple memory access operations, such traditional interface designs present a significant bottleneck to increasing memory performance. This is especially emphasized in processor-based systems designed for high-performance processors but that are limited by their memory subsystems. For example, increasing bus clock rates has often been the answer for improving memory performance. However, increasing bus clock rates eventually becomes impractical due to printed circuit board (PCB) limitations (e.g., trace length, capacitance, thermal ratings, etc.), which cause eventual edge skewing and signal breakdown.

Other drawbacks of traditional DRAM interface designs include how memory interfaces are used to communicate memory access requests and other commands. For example, to perform read or write operations, a memory controller first sends out part of an address called a row address, which a DRAM uses to identify a bank and read a corresponding row. The memory controller then sends out the rest of the address called a column address to identify a particular cache line in an open row. The memory controller sends separate control signals to differentiate between row addresses and column addresses. In addition, the memory controller must model the state of open rows in the DRAM which limits the use of DRAM to the specific type modeled by the controller. Thus, a DRAM relies on numerous communications from a memory controller for a significant amount of its operations. A drawback of such a traditional master-slave design is that as the number of memory chips or ranks inside a memory module increases, memory controller complexity also increases. As processors are provided with more memory controllers, increased complexity in memory controller design will require additional processor area and power budget. Another drawback is that DRAM organization is severely constrained by such a traditional master-slave design. For example, regardless of the process technology or memory capacity, a row access occurs using a first set of bits sent out by a memory controller, and any deviation from this will cause an incorrect or inoperable memory access or will result in additional delay as the memory module awaits a column address to perform the access.

Drawbacks of traditional DRAM interface designs are further seen in connection with optical interconnects. For example, due to the significant bandwidth increase provided by optics, the number of memory modules that can be connected to a memory controller is relatively high. A memory controller to keep track of all open banks in all DRAM modules would be significantly more complex. Thus, scalability using traditional DRAM interface designs may not be cost-effective or feasible.

Example methods, apparatus and articles of manufacture disclosed herein involve providing memories with bus interfaces configured to exchange information with memory controllers and with other memories (e.g., memory-to-memory transfers) using bus packet formats. The bus packets can be used to communicate address, data, and/or control information between one or more memory devices and one or more memory controllers on a single memory bus using point-to-point or broadcast communications. In some example implementations, the example memory bus interfaces described herein can be used in a multi-controller mode to enable connecting multiple memory controllers to one or more memory devices. An example memory bus interface described herein includes a command/request bus and a separate response bus. The command/request bus is used to communicate command information and memory access request information from one or more memory controllers to one or more memory devices. The response bus is used to communicate response information including acknowledgements and requested data between memory devices and memory controllers.

The bus packet communications used in connection with the memory bus interface described herein enable more efficient communications between memory controllers and memory devices and better use of memory access bandwidth internal to a memory device. For example, traditional DRAM memory interfaces are configured to serve only one memory controller and only one memory access request at a time. Although this enables a traditional memory controller to be in control of all memory access requests and most or all internal memory operations (e.g., pre-charge, self-refresh, low-power mode transitions, etc.), traditional memory interface architectures place a significant burden on the memory controllers and force all data transfers through the memory controllers. In contrast, the memory bus, bus packet communications, and internal structures disclosed herein enable a DRAM memory (or other types of memories) to concurrently serve memory controllers and other memory devices on the same memory bus and arbitrate between multiple pending memory access requests from one or more memory controllers or memory devices. That is, the memory device structures described herein can receive memory access requests via bus packets from memory controllers or memory devices, while internally arbitrating pending memory access requests and returning data to the same or other memory controller(s) or memory devices on the memory bus. In this manner, example methods, apparatus, and articles of manufacture disclosed herein enable memory interfaces having significantly less timing constraints than traditional memory interfaces and enable memory devices that can more efficiently access memory storage locations while concurrently receiving additional memory access requests or other bus packet communications from memory controllers or memory devices.

Using bus packets described herein, any memory can initiate a communication to another memory connected to the same bus without requiring intermediate communication of the copied data to the memory controller or a processor's cache. Checkpointing is an example use of such memory-to-memory transfers. Using traditional DRAM interface designs, data must be copied to a processor's cache when copying that data from one memory module to another memory module, which causes delays and pollutes the processor's cache leading to unnecessary cache misses. Using packet based communications as disclosed herein, a memory controller can initiate transfers directly between memory modules.

In addition, example methods, apparatus, and articles of manufacture disclosed herein enable memory devices to perform operations with relatively more autonomy than known memory devices. In this manner, memory bus utilization and memory access operations can be relatively more efficient than in known memory device implementations. To provide more autonomous operations of memory devices, example methods, apparatus, and articles of manufacture disclosed herein enable memory controllers to communicate hint information to memory devices that trigger autonomous action by the memory devices. Such hint information can be communicated via, for example, a command/request bus of a memory bus interface. Example hint information may be indicative of a memory controller not needing to access a memory device for some known or expected amount of time such that the memory device can enter a self-refresh state or low power mode (e.g., a standby or sleep mode) without delaying.

Upon receiving hint information, autonomous decision logic of the memory devices described herein can determine whether to act on or ignore the hint information without needing to receive further direction from the memory controller which communicated the hint information. For instance, a memory device implemented in accordance with example methods, apparatus, and articles of manufacture disclosed herein can arbitrate hints received from a memory controller in view of any internally executing or queued memory access operations yet to be fulfilled by the memory device. Through such arbitration, the memory device can autonomously determine whether it can or should act on any particular hint. For example, if a first memory controller determines that it will not be performing any memory accesses for at least the next 100 milliseconds (ms), the first memory controller generates a hint to indicate that the memory device is permitted to enter a self-refresh or lower power mode. If concurrently, the memory device receives a subsequent memory access request from the same or another memory controller or another memory device, the memory device can autonomously determine to ignore or defer the hint from the first memory controller because the memory device should remain active to service the subsequent memory access request. This is just one example of a type of hint that can be communicated to and processed by the memory devices disclosed herein. Other hint information can also be used as described in detail below.

Unlike traditional memory controllers and memory devices, in which memory operations management is centrally performed by the memory controllers, the hint information described herein enables off-loading, sharing, or shifting of significant portions of the memory operations management to memory devices. In this manner, memory device structures described herein enable a memory device to receive multiple memory access requests from multiple memory controllers and internally arbitrate how to handle such memory access requests for the memory controllers. Thus, example memory controllers disclosed herein are burdened with relatively less bus timing constraints because they can send memory access requests and hint information to memory devices and let the memory devices determine the timing for performing the requested or hinted operations.

Turning now to FIG. 1, an example memory interface configuration 100 shows a memory controller 102 operatively coupled to a memory 104. The memory controller 102 can be a standalone memory controller integrated circuit (IC) or an embedded memory controller implemented in a processor chip (e.g., fabricated on the same die or located in the same chip package as a processor core). In the illustrated example, the memory 104 is a DRAM memory. The DRAM memory 104 can be a single DRAM memory IC or a memory module including multiple DRAM memory ICs. In some example implementations, the DRAM memory 104 can be an embedded memory implemented in a processor chip. As shown, the memory interface configuration 100 includes a memory bus 106.

The memory bus 106 may be any number of bits wide and is used to communicate address, data, commands, and/or hint information between the memory controller 102 and the DRAM memory 104. When implemented as a memory module, each line of the memory bus 106 can be connected to multiple memory chips (or memory devices) of the memory module. The memory controller 102 can selectively communicate with separate ones of the memory chips based on chip identification information and/or address ranges as discussed in detail below.

Figure 3:
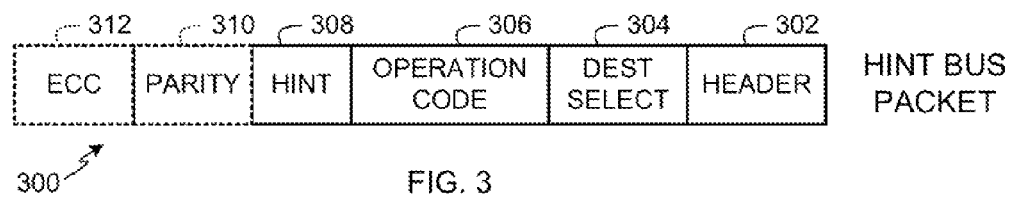
FIG. 3 depicts an example hint bus packet that can be used to communicate hint information from memory controllers to memory devices.
Figure 4:
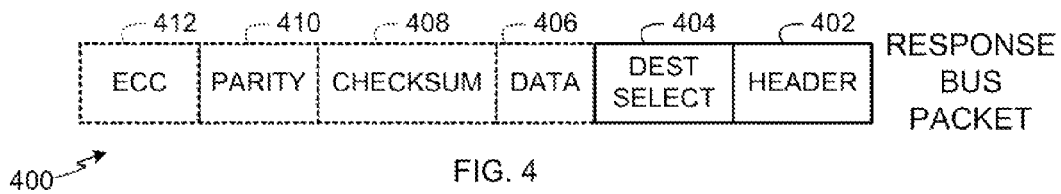
FIG. 4 depicts an example response bus packet that can be used to communicate responsive communications from memory devices to memory controllers.

In the illustrated example, the memory controller 102 and the DRAM memory 104 communicate via bus packets transmitted through the memory bus 106. A bus packet can contain one or more of hints 108, data 110, addresses 112, or operation codes 114. In some example implementations, packets may be used to communicate hint information alone, and separate read/write packets may be used to communicate memory access requests. Example bus packets are shown in FIGS. 2, 3, and 4.

Figure 2:
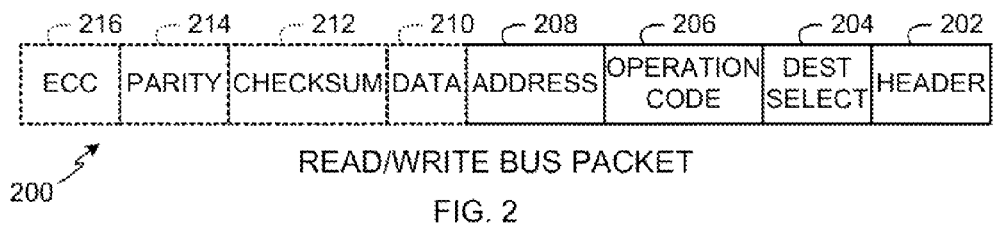
FIG. 2 depicts an example read/write bus packet that can be used to communicate read and/or write requests from memory controllers to memory devices.

Turning to FIG. 2, an example read/write bus packet 200 of FIG. 2 can be used to communicate memory access requests from memory controllers to memory devices. The bus packet 200 can also be used to communicate memory access requests between memory devices. In the illustrated example, the read/write bus packet 200 includes a header field 202, a destination select field 204, an operation code field 206, and an address field 208. The read/write bus packet 200 can also include a data field 210, a checksum field 212, a parity field 214, and an error correction code (ECC) field 216. For example, the data field 210, the checksum field 212, the parity field 214, and the ECC field 216 may be present when the read/write bus packet 200 is used to request a write operation. In such an instance, the data field 210 stores write data. In addition, the checksum field 212 stores a checksum value, the parity field 214 stores a parity value, and the ECC field 216 stores an ECC value, all of which can be used to detect any errors in the write data communicated in the data field 210 and/or other information in the read/write bus packet 200.

In the illustrated example, a read request message can include address bits and a burst length to reduce the number of read request messages that need to be communicated on the memory bus 106. In some example implementations, read request messages can also include stride and request interval values indicating a stride and interval with which burst data should be communicated to a requesting memory controller. Such stride and request interval values can be used in connection with streaming applications that typically need data at particular intervals or times. The use of stride and request interval values reduces the quantity of read request messages needing to be communicated by memory controllers. To halt or cancel a burst access, a memory controller can communicate a subsequent packet having an interrupt message. Such a packet can be in the form of a hint bus packet 300 described below in connection with FIG. 3 and carrying a non-ignorable interrupt instructing a memory to stop streaming data.

In the illustrated example, the header field 202 includes an identification of the requesting memory controller (e.g., the memory controller 102 of FIG. 1) that communicated the bus packet 200. The header field 202 can additionally or alternatively include any other information that would be suitable for communicating as header information. Such other information can be, for example, an indication of the type of information or operation being communicated (e.g., read/write/hint information).

The destination select field 204 can be used to communicate information indicative of a particular memory device to which a requesting memory controller (or other memory device) intends to send the bus packet 200. The destination select field 204 may be, for example, a memory device identifier that uniquely identifies a specific memory device on a bus (e.g., the memory bus 106). In some instances, the destination select field 204 is omitted and the address field 208 is used to indicate a target memory device. For example, if a memory device receives the read/write bus packet 200 and determines that the included address pertains to its memory range portion of a physical memory map (e.g., the physical memory map 816 of FIG. 8), the memory device tags or identifies the read/write bus packet 200 as relevant and further processes the bus packet 200.

The operation code field 206 is used to communicate codes indicating a requested operation. Example codes can be indicative of read operations, write operations, burst reads, etc.

The address field 208 can include one or more addresses and/or address offset information indicative of storage locations from which data is to be read or to which data is to be written.

The data field 210 can include data communicated by the memory controller 102 when the operation code field 206 indicates a write operation. This data may be, for example, data to be stored in the addressed memory. The checksum field 212 includes a checksum for data in the data field 210.

Turning to FIG. 3, an example hint bus packet 300 can be used to communicate hint information from memory controllers to memory devices or between memory devices. In the illustrated example, the hint bus packet 300 is shown as having a header field 302, a destination select field 304, an operation code field 306, a hint field 308, an optional parity field 310, and an optional ECC field 312. The parity field 310 and the ECC field 312 can be used to detect errors in the transmission of the hint bus packet 300. The header field 302 can be substantially similar or identical to the header field 202 of FIG. 2. The destination select field 304 can be substantially similar or identical to the destination select field 204 of FIG. 2. The operation code field 306 can be substantially similar or identical to the operation code field 206 of FIG. 2. In the illustrated example of FIG. 3, the operation code field 306 may include a no operation performed (NOP) code or some other code indicating that the bus packet 300 conveys hint information. The hint field 308 is used to convey hint information, which may be used by a memory controller to inform one or more memory devices of internal memory device operations that are permissible based on the memory controller's memory access needs (or lack thereof) for some subsequent amount of time. In some example implementations, the amount of time may be specified in the hint or may be pre-known by the memory device based on, for example, the type of hint received. In other example implementations, the memory device may not be made aware of an amount of time, but instead may perform the hinted operation (e.g., self-refresh, standby, low-power mode transition, etc.) until it is subsequently activated (e.g., through one or more control lines or a wake operation code in the operation code field 306 of a subsequent hint bus packet) or receives a subsequent memory access request.

Other types of hints can be used to control hybrid memory modules containing different types of memory technologies (e.g., a DRAM/memristor memory module or a DRAM/PCRAM memory module). For example, due to low write endurance ratings of non-volatile memories (e.g., flash memories, memristor memories, and PCRAM memories), a DRAM (or SRAM) used as a local cache or write buffer in a memory module can store frequently written or changing data that can be periodically written through to the non-volatile memories. Hint bus packets (e.g., the hint bus packet 300) can be communicated to a destination memory module before or following a write request to indicate that the write request contains either frequently written data (e.g., a frequently written data hint) or read-only data (e.g., a read-only data hint). In this manner, the destination memory module can elect to cache the data or write-through the data to the non-volatile memory. In addition, hints can be used to inform memory modules of memory access idle times during which write-through operations can be performed.

The example response bus packet 400 of FIG. 4 can be used to send a responsive communication from a memory device to a memory controller or to another memory device. In the illustrated example, the response bus packet 400 includes a header field 402, a destination select field 404, an optional data field 406, an optional checksum field 408, an optional parity field 410, and an optional ECC field 412. The header field 402 can be used to convey identification information of a communicating memory device, acknowledgement information, and/or any other information suitable as header information. The destination select field 404 can be used to communicate information indicative of a particular destination device (e.g., the memory controller 102) to which the response bus packet 400 is intended. The destination select field 404 may store, for example, a device identifier that uniquely identifies a specific device on a bus (e.g., the memory bus 106). In some instances when only two devices (e.g., the memory controller 102 and the memory 104 of FIG. 1) are present on a memory bus (e.g., the memory bus 106), the destination select field 404 may be omitted, ignored, or may always communicate the same information.

When the response bus packet 400 is used to return data responsive to a read request, the response bus packet 400 can include data retrieved from memory in the data field 406. In addition, the checksum field 408 is used to store a checksum, the parity field 410 is used to store a parity value, and the ECC field 412 is used to store an ECC value, all of which can be used to detect any errors in the data communicated in the data field 406 and/or other information in the response bus packet 400.

Returning to FIG. 1, a processor 116 is shown in communication with the memory controller 102. The processor 116 includes a cache memory 118 that functions as a temporary quick access storage area for a processor core of the processor 116. The cache memory 118 is formed of a plurality of cache lines, one of which is denoted as cache line 120. In some example processor system implementations, a size of a cache line (e.g., a 64-byte cache line, a 128-byte cache line, etc.) indicates the number of bytes that may be read from an external memory (e.g., a DRAM) to fill a width of a cache.

Figure 5:
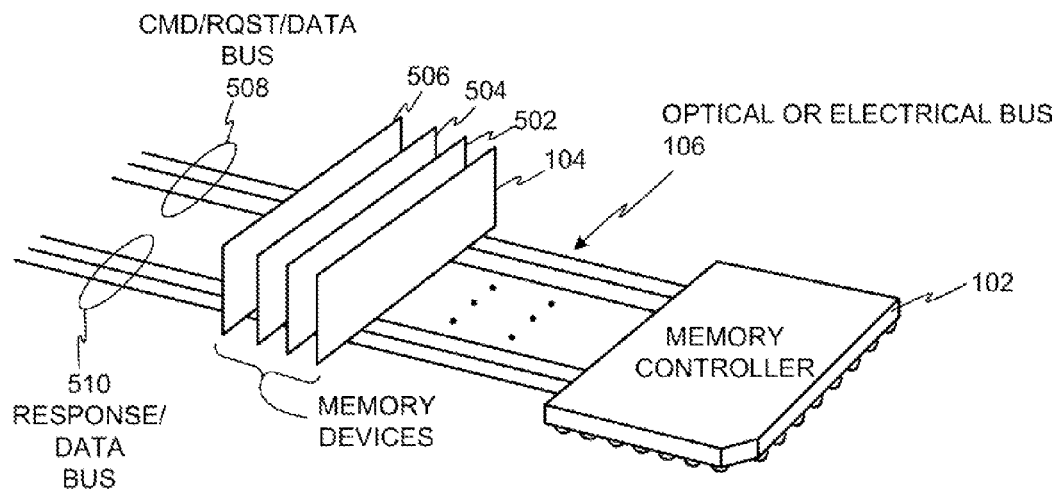
FIG. 5 depicts an isometric view of an example printed circuit board (PCB) configuration of a memory bus interconnecting a memory controller with a plurality of memory devices.

FIG. 5 depicts an isometric view of an example printed circuit board (PCB) configuration of the memory bus 106 (FIG. 1) interconnecting the memory controller 102 (FIG. 1) with a plurality of memory devices 104, 502, 504, and 506. In the illustrated example, the memory controller 102 can operate as a source or destination device and each of the memory devices 104, 502, 504, and 506 can also operate as source or destination devices. In the illustrated examples described herein, the memory devices 104, 502, 504, and 506 can communicate with one another to, for example, transfer memory contents therebetween. For example, during checkpointing processes, contents from one memory device can be transferred or copied to another memory device using memory-to-memory transfer operations.

Although not shown, additional memory controllers may also be placed in communication with the memory bus 106, and the memory bus 106 can be operated as a multi-source and multi-destination bus. In addition, the memory controllers and the memory devices can communicate bus packets on the memory bus 106 in point-to-point fashion when targeting specific memory controllers or memory devices or in broadcast fashion when targeting a plurality of devices.

In the illustrated example of FIG. 5, the memory bus 106 includes a command/request/data (CMD/RQST/DATA) bus 508 and a response/data bus 510. In the illustrated example, the CMD/RQST/DATA bus 508 forms an egress communication path used to communicate commands, memory access requests, write data, and/or hints from the memory controller 102 (and/or any other memory controllers on the memory bus 106) to one or more of the memory devices 104, 502, 504, and 506. In the illustrated example, the response/data bus 510 forms an ingress communication path used to communicate response information including acknowledgements and data from the memory devices 104, 502, 504, and 506 to the memory controller 102 (and/or any other memory controllers on the memory bus 106).

In the illustrated example of FIG. 5, the CMD/RQST/DATA bus 508 and the response/data bus 510 enable communications between the memory devices 104, 502, 504, and 506 to perform, for example, memory-to-memory transfers. For example, the memory device 104 may request access to the CMD/RQST/DATA bus 508 to transfer data to the memory device 502 or any of the other memory devices 504, 506. Similarly, any of the memory devices 104, 502, 504, and 506 may request access to the response/data bus 510 to send responses or data to another one of the memory devices 104, 502, 504, and 506. Memory-to-memory transfers between memory devices (e.g., between two or more of the memory devices 104, 502, 504, and 506) may be used to implement direct memory access (DMA) transfers between homogeneous memory technologies (i.e., memory devices of the same type of memory technology) or between heterogeneous memory technologies (i.e., memory devices of different types of memory technologies). In some examples, memory-to-memory transfers may be used to perform data write-through operations from memory technologies having high write endurance (e.g., DRAM memories) used to store frequently changing data to memory technologies having lower write endurance (e.g., flash memories, memristor memories, and/or PCRAM memories) used for storing longer-term persistent data.

The memory bus 106 can be implemented using electrical interconnects or optical interconnects. Electrical interconnects can be formed on a PCB using known techniques. Optical interconnects can be formed, for example, as described in U.S. patent application Ser. No. 11/873,325, filed on Oct. 16, 2007, assigned to Hewlett-Packard Development Company, L.P., and titled "Optical Interconnect System Providing Communication Between Computer System Components," which is hereby incorporated herein by reference in its entirety.

Figure 6:
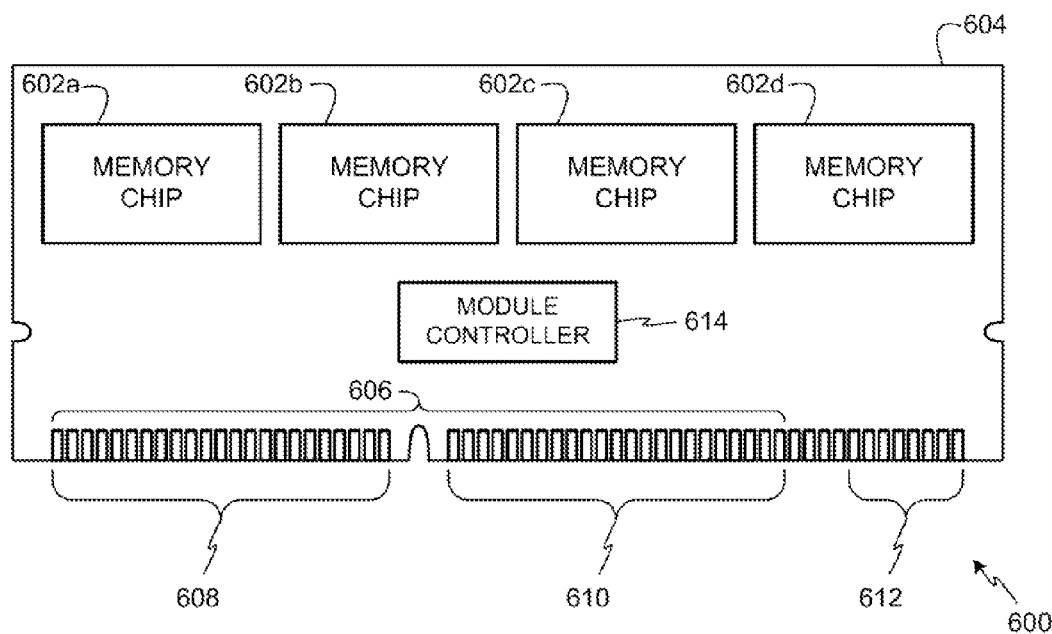
FIG. 6 depicts an example PCB in-line memory module having a plurality of memory chips and a memory bus interface to communicate with the memory chips.
Figure 12:
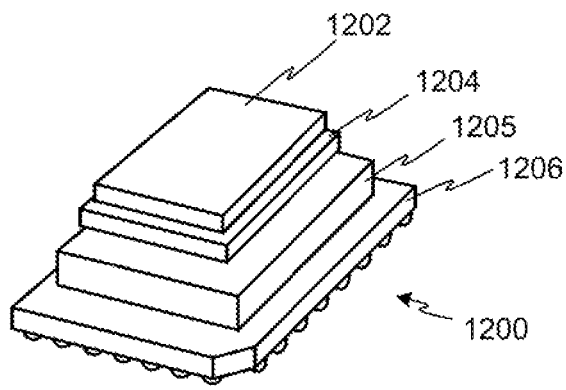
FIG. 12 depicts an example 3D chip stack memory module.

Turning to FIGS. 6 and 12, the example memory modules 600 and 1200 depicted therein can be used to implement example methods, apparatus, and/or articles of manufacture disclosed herein. In the illustrated example of FIG. 6, a DRAM PCB in-line memory module 600 (e.g., a dual in-line memory module (DIMM)) is implemented as a multi-chip memory module including four memory chips 602a-d mounted on a PCB 604. The DRAM PCB in-line memory module 600 may be advantageously used in optical interface systems in which the memory module 600 is connected to other subsystems (e.g., other memory modules and/or memory controllers) via optical lines. Alternatively, the memory module 600 may also be used in electrical interface systems. To interconnect with the memory bus 106 (FIGS. 1 and 5), the memory module 600 is provided with memory bus interface pads 606. Each line of the memory bus interface pads 606 may be in communication with one or more of the memory chips 602a-d. In this manner, the memory bus interface pads 606 form a local bus on the memory module 600 to exchange communications between a main memory bus (e.g., the memory bus 106) and the memory chips 602a-d using communications substantially similar or identical to the communications described above in connection with FIGS. 1-5. The memory module 600 can operate using source synchronous clocking or external clocking.

As shown in FIG. 6, the memory bus interface pads 606 are divided into CMD/RQST/DATA bus interface pads 608 to communicate with the CMD/RAST/DATA bus 508 of FIG. 5 and response/data bus interface pads 610 to communicate with the response/data bus 510 of FIG. 5. The memory module 600 is also provided with power and ground pads 612 for interconnecting power and ground to the memory chips 602a-d.

Although the memory module 600 is shown as having four memory chips, example methods, apparatus, and articles of manufacture disclosed herein may be implemented in memory modules having fewer or more chips. In addition, in some example implementations, the memory bus interface pads 606 can alternatively be implemented using optical interconnect interfaces and the memory module 600 may be provided with local waveguides for routing optical signals between the optical interconnect interfaces and on-board photo-detectors or directly between the optical interconnect interfaces and the memory chips 602a-d.

The memory module 600 also includes a module controller 614 in communication between the memory bus 106 and the memory chips 602a-d to filter and arbitrate messages from memory controllers and other memory modules or devices and exchange information between the memory bus 106 and the memory chips 602a-d. An example implementation of the module controller 614 is described below in connection with FIG. 7.

In some example implementations, the memory module 600 may be implemented as a multiple memory-type module on which memories of different technology types can be provided. For example, the memory chip 602a may be a volatile SDRAM-type memory and the memory chips 602b-d may be non-volatile memristor-type memories. The SDRAM-type memory may be used as a local cache for frequently written data because of its low data access times and high write endurance ratings (e.g., write cycle rating). Data from the SDRAM-type memory can be periodically written through to the non-volatile memristor-type memories, which can typically have higher data access times and lower write endurance ratings. In other example implementations, the memory chips 602b-d could alternatively be implemented using PCRAM, flash memory, or any other type of memory.

In some examples, each of the memory chips 602a-d could be implemented using a 3D chip stack in which two or more memory dies (e.g., of homogeneous or heterogeneous memory technology types) are stacked (e.g., similar to the 3D stack structure shown in FIG. 12). Alternatively, only select ones of the memory chips 602a-d may be implemented using 3D chip stacks.

An example 3D chip stack memory module 1200 is shown in FIG. 12. The 3D chip stack memory module 1200 may be advantageously used in electrical interface systems in which the memory module 1200 is connected to other subsystems (e.g., other memory modules and/or memory controllers) via electrical lines. Alternatively or additionally, the memory module 1200 may be used in optical interface systems. The example 3D chip stack memory module 1200 of FIG. 12 includes a first IC die 1202 stacked on a second IC die 1204, which is stacked on a third IC die 1205. The IC dies 1202, 1204, and 1205 are carried on a ball grid array (BGA) chip package 1206. Although the chip package 1206 is shown as a BGA chip package in the illustrated example, any other suitable type of chip package may be used to implement the example 3D chip stack memory module 1200. In the illustrated example, the first IC die 1202 is a SDRAM memory core and the second IC die 1204 can be another SDRAM memory core or any other type of memory (e.g., memristor memory, SRAM, flash memory, PCRAM, etc.) or IC (e.g., a processor, a controller, etc.). In example implementations in which an SDRAM die (or any other memory technology die) is stacked on a processor or controller die, address, control, and data lines of the SDRAM die can be routed directly to the processor or controller die internal to the chip stack package. In such implementations, memory access external from the chip stack package might not occur. Alternatively or additionally, to enable external memory access, address, control, and data lines of the memory IC dies can be routed to external chip interfaces (e.g., BGA pads, surface mount pads, chip leads, etc.). In some examples, a memory module controller may be stacked with multiple memory die. For example, in the illustrated example of FIG. 12, the IC die 1205 may be a module controller (e.g., similar or identical to the module controller 614). Although the 3D chip stack memory module 1200 is shown as a BGA package, other types of packages may be used.

Figure 7:
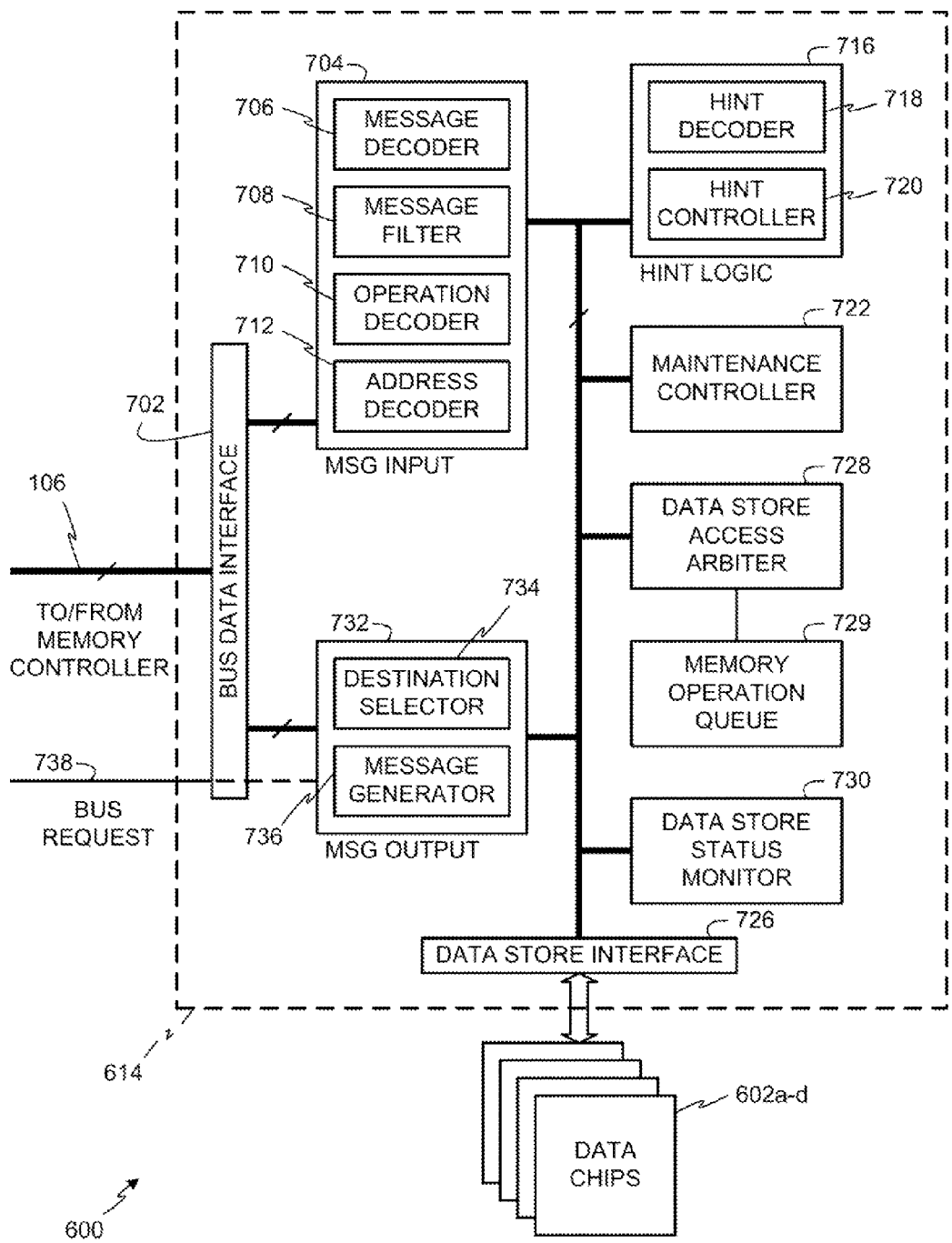
FIG. 7 is a block diagram of a memory module controller that can be used to communicate via a memory bus interface and process hint information.

FIG. 7 is a block diagram of the module controller 614 of FIG. 6. The different portions of the module controller 614 described below can be implemented as integrated circuits within a chip or IC die. The chip or IC die containing the module controller 614 can then be mounted electrically or optically on a PCB (e.g., the PCB 604 of FIG. 6) and/or a 3D chip stack structure (e.g., the 3D chip stack memory module 1200 of FIG. 12) having one or more memory devices to exchange information between the memory bus 106 (FIGS. 1 and 5) and corresponding memory chips (e.g., the memory chips 602a-d of FIG. 6). Although the module controller 614 is described below in connection with the diagram of FIG. 7, other example implementations are likewise appropriate. For example, additional structures may be added, and/or some of the portions of the module controller 614 depicted in FIG. 7 may be eliminated or combined with other portions.

In the illustrated example, the module controller 614 includes a bus data interface 702 to communicatively couple the module controller 614 to the memory bus 106 (FIGS. 1 and 5). The bus data interface 702 may include tri-state bi-directional buffers to enable receiving/sending information on the memory bus 106 while the module controller 614 is actively communicating on the memory bus 106, and to enable placing bus pins or pads at a high-impedance tri-state level when the module controller 614 is not actively communicating on the memory bus 106.

The bus data interface 702 may also include a clock interface in example implementations in which the module controller 614 operates using external clocking. Otherwise, if the module controller 614 operates using source synchronous clocking, the module controller 614 can include a clock source (not shown).

To decode and filter messages or bus packets received from the memory bus 106, the module controller 614 is provided with a message input subsystem 704. The message input subsystem 704 includes a message decoder 706, a message filter 708, an operation decoder 710, and an address decoder 712. In the illustrated example, the message decoder 706 parses bus packets (e.g., the bus packets 200 and 300 of FIGS. 2 and 3) to identify information in different fields (e.g., the fields 202, 204, 206, 208, 210, and 212 of FIG. 2 and/or the fields 302, 306, and 308 of FIG. 3) of the bus packets.

The message filter 708 filters received bus packets by identifying which bus packets are relevant to the memory module 600 (e.g., relevant to the memory chips 602a-d in communication with the module controller 614) and which bus packets can be ignored (e.g., they are relevant to other memory devices on the memory bus 106). This can be done by snooping the headers of packets. For example, the message filter 708 can retrieve memory device identification information (e.g., from the destination select field 204 of FIG. 2 or the destination select field 304 of FIG. 3) from header information (e.g., the headers 202, 302, 402 of FIGS. 2-4) and compare the retrieved memory device identification information to a unique identification value of the memory module 600 to determine whether bus packets are relevant to the memory module 600. In some instances, a destination select field may be blank or contain a general code indicating that the bus packet is a broadcast packet intended for all memory devices on the same memory bus. If a bus packet is relevant to the memory module 600, the message filter 708 can generate an indication that the received bus packet should be processed (i.e., should not be ignored) by the module controller 614. Otherwise, if the message filter 708 determines that a bus packet is not relevant based on snooping header information, the remainder of the packet can be filtered out at the bus interface 702.

The operation decoder 710 retrieves and identifies operation codes from received bus packets (e.g., from the operation code fields 206 and 306 of FIGS. 2 and 3). The address decoder 712 retrieves and decodes addresses from received bus packets (e.g., from the address field 208 of FIG. 2). For example, if the memory chips 602a-d operate internally using row and column addresses, the address decoder 712 can separate address information into row and column addresses.

To process hint information, the module controller 614 is provided with a hint logic subsystem 716 that includes a hint decoder 718 and a hint controller 720. In the illustrated example, the hint decoder 718 receives hint information extracted from bus packets by the message decoder 706 and decodes the hint information to identify different types of hints. The hint controller 720 analyzes the identified hints to determine whether the hints should be acted on or ignored. The hint controller 720 bases such decisions on different factors (or criteria) including whether the memory module 600 is executing a pending memory access request, whether memory access requests are queued up, and/or whether the memory module 600 is or will be processing some other memory operation that may prevent it from acting on a hint. The hint controller 720 can also drop irrelevant hints (e.g., a sleep hint received when memory chips are already in a sleep mode).

To control the performance of internal maintenance operations, the module controller 614 is provided with a maintenance controller 722. In the illustrated example, the maintenance controller 722 determines when to implement pre-charging of bit cells (to enable memory reads), self-refresh operations, low-power mode transitions, wake transitions, etc. In some instances, the maintenance controller 722 can work in cooperation with the hint logic subsystem 716 to implement certain internal maintenance operations during opportunities identified by the hint logic subsystem 716 based on received hint information. For example, if a received hint indicates that a particular memory controller will not access the memory module 600 for a particular time period, length of time, or duration, the hint controller 720 can identify an opportunity to the maintenance controller 722 to perform a self-refresh operation, to enter a low-power mode, and/or to perform other maintenance operations.

To store information, the module controller 614 is provided with a memory device interface 726, which is in communication with the memory chips 602a-d in the illustrated example. The memory device interface 726 can include bi-directional buffers for reading data from and writing data to the memory chips 602a-d and for providing address information to the memory chips 602a-d.

To arbitrate the servicing of memory access requests, the module controller 614 is provided with a data store access arbiter 728. The data store access arbiter 728 can store and/or access a memory operation queue 729 of memory access requests communicated to the memory module 600 and allow servicing of those requests in an orderly manner such as on a first in, first out priority basis. In the illustrated example, the data store access arbiter 728 also manages and monitors the memory operation queue 729 to determine when the quantity of queued requests exceeds a threshold indicative of when no further memory access requests can be added to the queue 729. For instance, this can happen when the queue is full and can no longer buffer incoming requests. When no further access requests can be added to the memory operation queue 729, the data store access arbiter 728 of the illustrated example causes a message output subsystem 736 to respond to subsequent memory access requests received via the bus data interface 702 with negative acknowledgements until the quantity of requests in the queue 729 falls below the threshold. The negative acknowledgements can indicate to one or more requesting device(s) (e.g., the memory controller 102 of FIGS. 1, 5, and 8 or any of the memory devices 104, 502, 504, and 506 of FIGS. 1 and 5) that the memory access requests cannot be granted. In some examples, the negative acknowledgements also indicate that the requesting device(s) should re-send the memory access request to the memory module 600 at some later time (e.g., a time that may or may not be specified by the data store access arbiter 728 or the module controller 614). In some examples, the negative acknowledgements cause the requesting device(s) to resend the memory access request to the memory module 600 at some later time (e.g., a time that may or may not be specified by the data store access arbiter 728 or the module controller 614).

To monitor the status of the memory chips 602*a-d*, the module controller 614 is provided with a data store status monitor 730. The data store status monitor 730 tracks when operations are being performed on the memory chips 602*a-d* including read/write operations, self-refresh operations, pre-charge operations, power down operations, etc. The data store status monitor 730 tracks when the memory chips 602*a-d* are in a sleep mode, standby, or other low-power mode. Based on the activity tracked in the memory chips 602*a-d*, the data store status monitor 730 can determine whether the memory chips 602*a-d* are busy or idle and whether queued or recently received operations can be performed immediately or need to be delayed until other operations are completed. In the illustrated example, the data store status monitor 730 can exchange information with the data store access arbiter 728, the maintenance controller 722, and the hint logic subsystem 716.

To generate messages or bus packets for transmitting on the memory bus 106, the module controller 614 is provided with a message output subsystem 732. For example, the message output subsystem 732 may generate the response bus packet 400 of FIG. 4 for communicating data to a memory controller (e.g., the memory controller 102 of FIGS. 1 and 5) in response to a read request from that memory controller. The message output subsystem 732 includes a destination selector 734 and a message generator 736. The destination selector 734 selects unique identifications of destination devices (e.g., the memory controller 102 of FIGS. 1 and 5) to which bus packets are to be communicated and stores unique identifications in destination select fields (e.g., the destination select field 404 of FIG. 4) of the bus packets. The destination selector 734 can store a data structure of device identifier codes, each of which corresponds to a respective device connected to the module controller 614 via the memory bus 106. In some example implementations, the destination selector 734 can receive device identifier codes from the data store access arbiter 728 in connection with the message output subsystem 732 receiving data from the data store interface 726. In this manner, a device identifier code received from the data store access arbiter 728 could be used to indicate the device that requested data received from the data store interface 726.

The message generator 736 forms the response bus packet 400 by, for example, concatenating information from the header field 402, the destination select field 404, the data field 406, and the checksum field 408. In some example implementations, the message generator 736 may be configured to generate checksums, parity values, and ECC values for read data, while in other example implementations, the data store interface 726 may be configured to generate such information.

To request access to the memory bus 106, the module controller 614 of the illustrated example is provided with a bus request line 738. In the illustrated example of FIG. 7, the bus request line 738 is external to the module controller 614 and is configured to be connected to the memory controller 102 to request that the memory controller 102 grant the memory module 600 access to the memory bus 106. In this manner, the memory module 600 can send data and/or messages to other devices (e.g., to the memory controller 102 and/or to other memory devices such as the memory devices 104, 502, 504, and/or 506 of FIGS. 1 and 5) via the memory bus 106 without causing collisions or bus contention on the memory bus 106. In the illustrated example of FIG. 7, the bus request line 738 is internally connected to the message output subsystem 732. In this manner, when the message output subsystem 732 is ready to communicate a bus packet on the memory bus 106, the message output subsystem 732 of the illustrated example causes a signal assertion on the bus request line 738 to request access to the memory bus 106. In some examples, the bus request line 738 is a bi-directional line via which the memory controller 102 can respond to grant memory bus access. In other examples, the bus request line 738 is a unidirectional output line from the module controller 614 and the memory controller 102 sends bus access grant responses to the module controller 614 via the memory bus 106.

In some examples in which multiple memory modules (e.g., the memory devices 104, 502, 504, and 506 of FIGS. 1 and 5) are connected to the same memory bus 106, the other memory modules are also provided with respective bus request lines similar or identical to the bus request line 738 of FIG. 7 to allow the other memory modules to request access to the memory bus 106.

Figure 8:
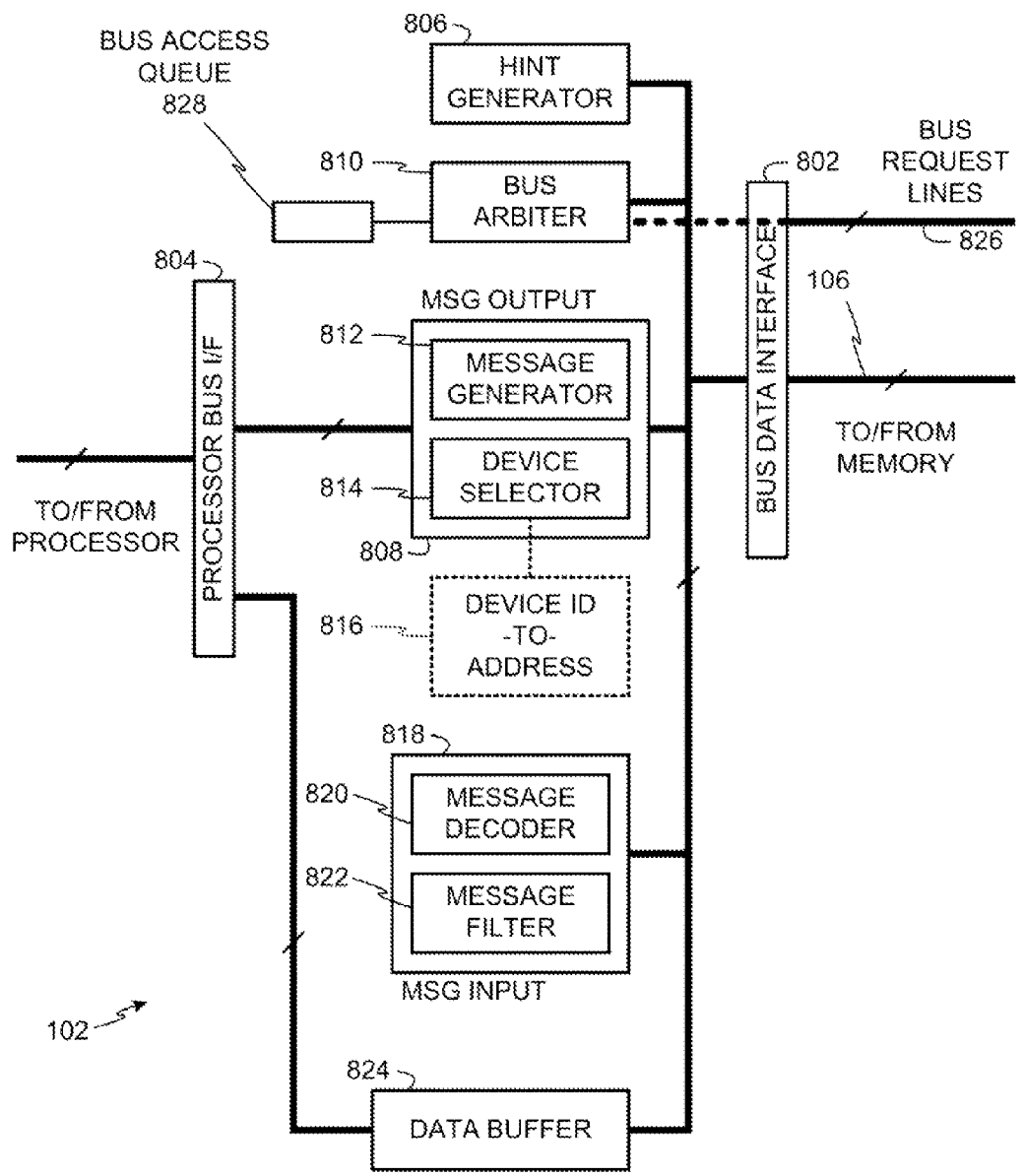
FIG. 8 is a diagram of a memory controller configured to communicate with the DRAM of FIGS. 1, 5, and 7 via the memory bus interface of FIGS. 1, 5, and 7.

FIG. 8 is a block diagram of the example memory controller 102 (FIGS. 1 and 5). The different portions of the example memory controller 102 described below can be implemented as integrated circuits within a single IC die as a stand-alone memory controller or as a memory controller embedded in a processor IC die. Alternatively, some portions of the memory controller 102 can be implemented as integrated circuits on one or more separate integrated circuit dies. Additionally or alternatively, the memory controller 102 may be implemented using any combination(s) of application specific integrated circuit(s) (ASIC(s)), programmable logic device(s) (PLD(s)), field programmable logic device(s) (FPLD(s)), discrete logic, hardware, firmware, etc. Also, the memory controller 102 may be implemented as any combination(s) of any of the foregoing techniques, for example, any combination of firmware, software, discrete logic and/or hardware. Although the memory controller 102 is described below in connection with the diagram of FIG. 8, other example implementations may include additional and/or alternative structures. For example, some of the portions of the memory controller 102 depicted in FIG. 8 may be eliminated or combined with other portions.

In the illustrated example, the memory controller 102 includes a bus data interface 802 to communicatively couple the memory controller 102 to the memory bus 106 (FIGS. 1, 5, and 7). The bus data interface 802 may include tri-state bi-directional buffers to enable receiving/sending information on the memory bus 106 while the memory controller 102 is actively communicating on the memory bus 106, and to enable placing bus pins or pads at a high-impedance tri-state level when the memory controller 102 is not actively communicating on the memory bus 106. To communicate with a processor (e.g., the processor 116 of FIG. 1), the memory controller 102 is provided with a processor bus interface 804.

To generate hints, the memory controller 102 is provided with a hint generator 806. The hint generator 806 can generate hints based on the receipt of memory access requests from a processor (e.g., the processor 116 of FIG. 1) or based on status information received from the processor. For example, if a processor connected to the memory controller 102 has not sent any memory access requests to the memory controller 102 or is not in an active operating mode (e.g., is idle or in a low-power mode), the memory controller 102 can generate a hint informing one or more memory devices that the memory controller 102 will not access the memory device(s) for a particular time period, length of time, or duration (e.g., thereby permitting the memory device(s) to perform one or more internal processes such as self-refreshing, entering a low-power mode, etc.). In some example implementations, the hint generator 806 can receive different control or status information from a connected processor indicating the operating mode of the processor such as active, standby, sleep, deep-sleep, powered-off. In this manner, the hint generator 806 can generate hint information based on the operating modes of the processor. For instance, if the processor is in a deep-sleep mode, the hint generator 806 can generate a hint informing one or more memory devices that they can transition into a very low-power mode (e.g., a deep-sleep mode).

To arbitrate communications exchanged on the memory bus 106, the memory controller 102 is provided with a bus arbiter 810. In the illustrated example, the bus arbiter 810 can be used to control access to the memory bus 106 and identify when the memory bus 106 is available to transmit communications (e.g., bus packets) and when the memory bus 106 is being used by another device. When a memory module or memory controller cannot store an incoming request, the bus arbiter 810 can send out a negative acknowledgement message to the source device asking for redelivery. Alternatively, the bus arbiter 810 can keep track of requests pending at various memory modules on the memory bus 106 and ensure the availability of input buffers of those memory modules before allowing the memory controller 102 to issue a request.

The bus arbiter 810 may be implemented for use on an electrical-based memory bus or an optical memory bus. An example optical memory bus for which the bus arbiter 810 can be used involves use of an optical token channel in which a token is circulated on a bus for use in claiming exclusive use of the bus at different times by different devices. In example implementations using such an optical token channel memory bus, the bus arbiter 810 can track when a token is circulating on the memory bus 106 to identify when the bus is available and when it is in use by another device.

To generate messages or bus packets for transmitting on the memory bus 106, the memory controller 102 is provided with a message output subsystem 808. For example, the message output subsystem 808 may generate the read/write bus packet 200 of FIG. 2 for communicating data access requests to one or more memory devices (e.g., the DRAM memory 104 of FIGS. 1, 5, and 7) and the hint bus packet 300 of FIG. 3 for communicating hints to one or more memory devices. The message output subsystem 808 includes an address generator (not shown), a message generator 812, and a device selector 814.

The message generator 812 forms bus packets (e.g., the read/write bus packet 200 and/or the hint bus packet 300). In some example implementations, the message generator 812 may be configured to generate checksums, parity values, and error correction codes for write data (e.g., data in the data field 210 of FIG. 2), while in other example implementations, checksums, parity values, and error correction codes may be provided by a processor connected to the memory controller 102. In addition, the message generator 812 can split an address into two or more separately transferrable portions so that a lengthy address can be transferred to a memory device using two or more separate bus packets.

The device selector 814 selects a unique identification of a memory device (e.g., one of the memory devices 104, 502, 504, and 506 of FIG. 5) to which a bus packet is to be communicated and stores the unique identification in a chip/device select field (e.g., the destination select field 204 of FIG. 4) of the bus packet. The device selector 814 can store a data structure of memory device identifier codes, each of which corresponds to a respective memory device connected to the memory controller 102 via the memory bus 106. In some example implementations, the device selector 814 can receive memory device identifier codes based on different physical memory slots occupied by different memory devices. Alternatively, the device selector 814 may be configured to assign unique identifier codes to each memory device detected on the memory bus 106. In this manner, the device selector 814 can deterministically identify specific memory devices for communicating corresponding bus packets.

In some example implementations, the device selector 814 can identify a destination device based on a physical address of a memory request. For example, the memory controller 102 can include a device ID-to-address data structure 816 storing cross-references between device ID's and respective memory address ranges. The device selector 814 can use the device ID-to-address data structure 816 to identify a destination device based on an address in a memory access request.

To decode and filter messages or bus packets received from the memory bus 106, the memory controller 102 is provided with a message input subsystem 818. The message input subsystem 818 includes a message decoder 820 and a message filter 822. In the illustrated example, the message decoder 820 parses bus packets (e.g., the response bus packet 400 of FIG. 4) to identify information in different fields (e.g., the fields 402, 404, 406, and 408 of FIG. 4) of the bus packets.

The message filter 822 filters received bus packets by identifying which bus packets are relevant to the memory controller 102 and which bus packets can be ignored (e.g., they may be relevant to other devices on the memory bus 106 but are not relevant to the memory controller associated with the message filter 822). For example, the message filter 822 can retrieve device identification information (e.g., from the destination select field 404 of FIG. 4) from bus packets and compare the retrieved device identification information to a unique identification value of the memory controller 102 to determine whether bus packets are relevant to the memory controller 102. If a bus packet is relevant to the memory controller 102, the message filter 822 can generate an indication that the received bus packet should be processed (i.e., should not be ignored) by the memory controller 102.

To buffer data from a processor or from memory devices, the memory controller 102 is provided with a data buffer 824. In the illustrated example, the data buffer 824 stores data received from a processor to be written to memory in response to a write request and stores data from memory to be communicated to a processor in response to a read request. When generating a write request bus packet, the message generator 812 can retrieve corresponding data from the data buffer 824 and store the data in a data field (e.g., the data field 210) of the write request bus packet. When receiving a response bus packet (e.g., the response bus packet 400 of FIG. 4), the message decoder 820 can parse data from a data field (e.g., the data field 406 of FIG. 4) of the response bus packet and store the data in the data buffer 824 for subsequent communication to the requesting processor.

To receive requests to access the memory bus 106, the memory controller 102 of the illustrated example is provided with bus request lines 826. In the illustrated example of FIG. 8, the bus request lines 826 are external to the memory controller 102 and are configured to be connected to memory devices or memory modules (e.g., the memory devices 104, 502, 504, and 506 of FIGS. 1 and 5) or other memory controllers or processors that request access to the memory bus 106 to exchange communications with the memory controller 102 and/or with one another via the memory bus 106. In this manner, the memory devices or memory modules and/or the memory controller 102 can send data and/or messages to one another via the memory bus 106 without causing collisions or bus contention on the memory bus 106. If there is more than one memory controller connected to the memory bus 106, the memory controller having a bus arbiter (e.g., the bus arbiter 810), is the master memory controller. In some examples, all of the memory controllers may have a bus arbiter, but only the memory controller designated as the master memory controller will enable its bus arbiter and the slave memory controllers will disable or not use their bus arbiters so that multiple memory controllers will not contend with managing use of the memory bus 106. In the illustrated example of FIG. 8, the bus request lines 826 are internally connected to the bus arbiter 810. In this manner, when a connected memory module signals a bus request via a respective one of the bus request lines 826, the bus arbiter 810 of the illustrated example determines whether to and/or when to grant access to the memory bus 106. For example, the bus arbiter 810 may grant access to the memory bus 106 based on statuses of the memory bus 106 such as statuses of when the memory bus 106 is busy (e.g., the memory bus 106 is being used by another memory controller, a memory module or memory device, a processor, etc.). In some examples, the bus arbiter 810 may include or be in communication with a bus access queue 828 to store bus access requests and grant memory bus access based on the queued requests. In some examples, the bus request lines 826 are bi-directional lines via which the memory controller 102 can respond to grant memory bus access. In other examples, the bus request lines 826 are unidirectional input lines into the memory controller 102 and the memory controller 102 sends bus access grant responses to requesting devices via the memory bus 106.

Figure 9A:
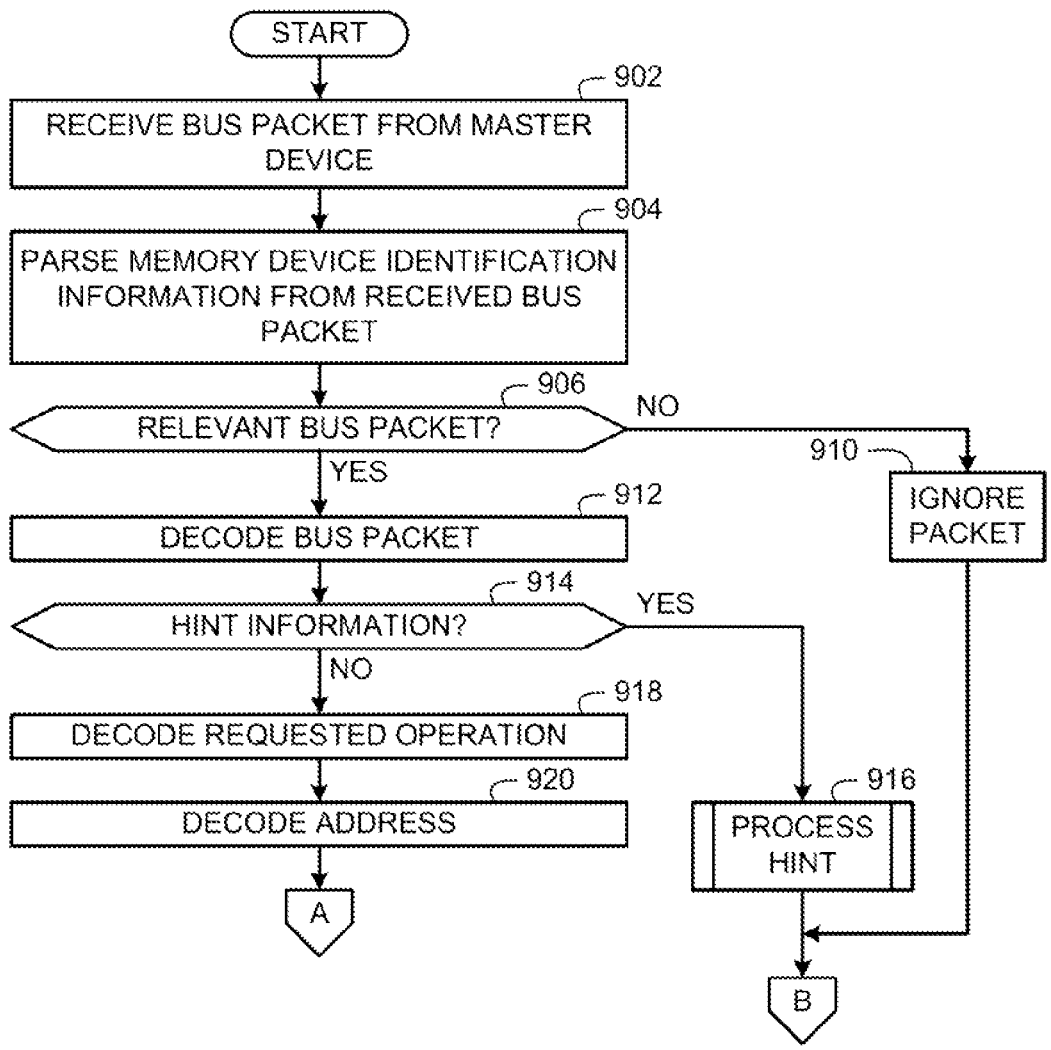
FIGS. 9A and 9B depict a flow diagram of an example process that can be executed by memory modules to process memory access requests and hint information.
Figure 9B:
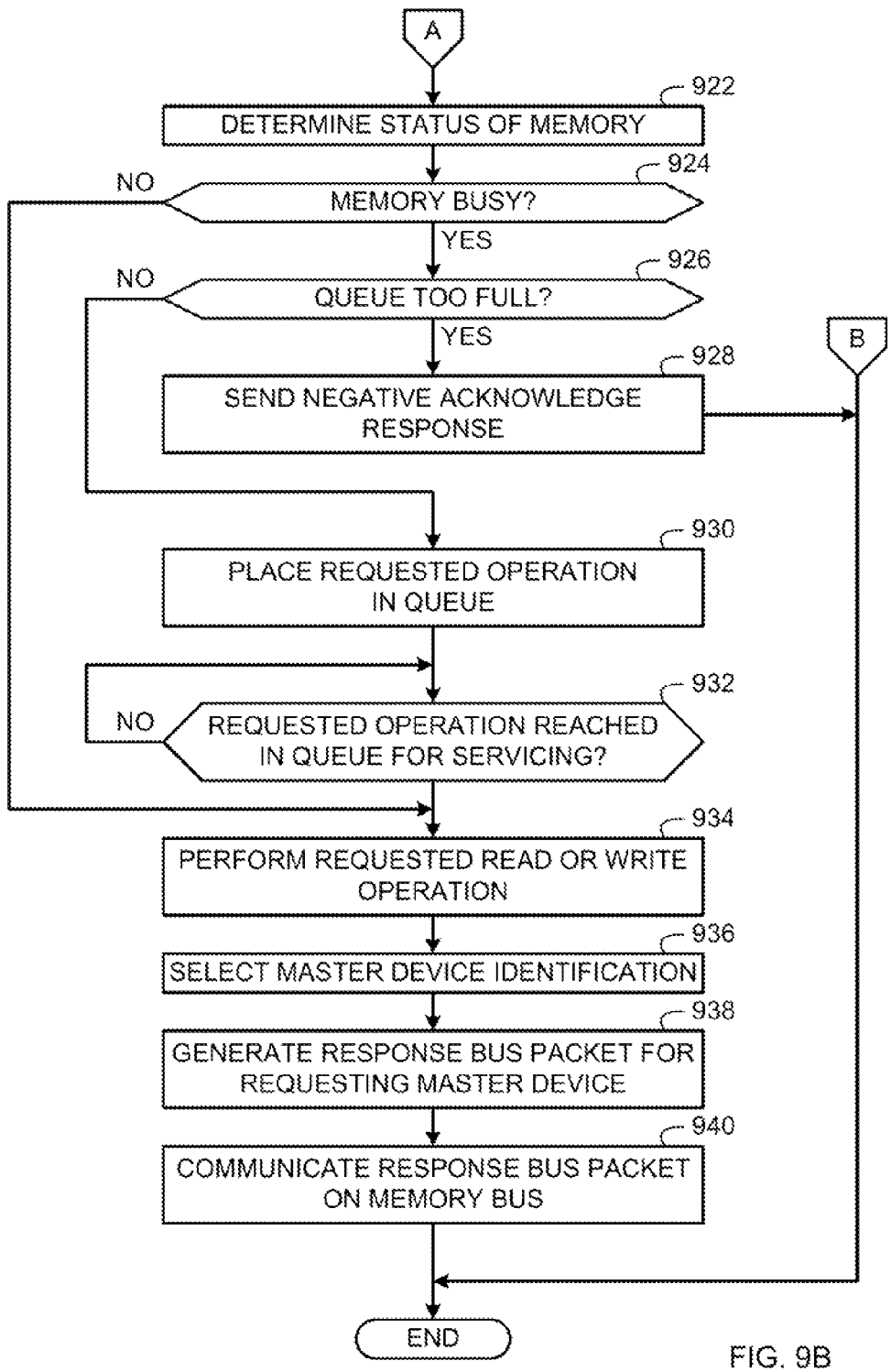

FIGS. 9A and 9B depict a flow diagram of an example process that can be executed by memory modules to process memory access requests and hint information. The example process is described in connection with the memory module 600 of FIGS. 6 and 7, but may alternatively be implemented using other memories (e.g., the memory devices 502, 504, and 506 of FIG. 5 and/or the memory module 1200 of FIG. 12) and/or other types of memories. In addition, although FIGS. 9A and 9B are described below in connection with the flow diagram as depicted, some examples employ different operations in addition to or instead of the operations of FIGS. 9A and 9B. For instance, some operations of FIGS. 9A and 9B may be omitted or combined with other operations or performed in a different order or in parallel with other operations.

Initially, the message input subsystem 704 (FIG. 7) receives a bus packet from a source device such as, for example, the memory controller 102 (FIGS. 1, 5, and 8) (block 902) (FIG. 9A). In some examples, the source device may be implemented using any memory device (e.g., any of the memory devices 104, 502, 504, and 506 of FIGS. 1 and 5) on the same memory bus (e.g., the memory bus 106) as the example memory module 600 and request to perform an inter-memory-module memory-to-memory data transfer to, for example, write data to the memory module 600. In such examples, the bus packet may be received via the bus data interface 702. In other examples, the source device may be a memory chip (e.g., one of the memory chips 602a-d of FIG. 6) or IC die (e.g., one of the IC dies 1202, 1204, 1205 of FIG. 12) located on the same memory module as the message input subsystem 704, and the bus packet may contain a request to perform an intra-memory-module memory-to-memory data transfer to, for example, write data between memories within the same memory module 600 of FIG. 6 or within the same memory module 1200 of FIG. 12. In such examples, the bus packet may be received via the data store interface 726. Although block 902 is described as involving receipt of a bus packet, a communication received at block 902 may be received using a communication other than a bus packet communication.

The message decoder 706 (FIG. 7) parses the memory device identification information from the received bus packet (block 904). For example, the message decoder 706 can retrieve a memory device identifier from a device select field (e.g., the destination select field 204 of FIG. 2 or the destination select field 304 of FIG. 3). The message filter 708 (FIG. 7) determines whether the received bus packet is relevant to the memory module 600 (block 906) by, for example, comparing the memory device identifier retrieved from the bus packet with a memory device identifier of the memory module 600. In some instances, a destination select field may be blank or contain a general code indicating that the bus packet is a broadcast packet intended for all memory devices on the memory bus 106. In other example implementations, the message filter 708 determines whether the bus packet is relevant based on whether an address communicated in the bus packet (and decoded by the address decoder 712 (FIG. 7)) falls within a memory address range assigned to the memory module 600.

If the received bus packet is not relevant (block 906), the module controller 614 ignores the bus packet (block 910). However, if the received bus packet is relevant (block 906), the message decoder 706 continues decoding the bus packet (block 912). The operation decoder 710 (FIG. 7) determines whether the bus packet contains hint information (block 914). For example, an operation code in an operation code field (e.g., the operation code field 306 of FIG. 3) or a code in a header field (e.g., the header field 302 of FIG. 3) can be used to identify the bus packet as a hint bus packet (e.g., the hint bus packet 300 of FIG. 3).

If the operation decoder 710 determines that the bus packet does contain hint information (block 914), the module controller 614 processes the hint information (block 916). An example process that can be used to implement block 916 is described below in connection with FIG. 10.

If the operation decoder 710 determines that the bus packet does not contain hint information (block 914), the operation decoder 710 decodes the requested operation from the bus packet (block 918), for example, based on an operation code in an operation code field (e.g., the operation code field 202 of FIG. 2). The requested operation can be a read operation, a write operation, or some variation thereof (e.g., a burst read, a page-mode read, etc.).

The address decoder 712 (FIG. 7) decodes an address from the bus packet (block 920) (e.g., an address stored in the address field 208 of FIG. 2). In example implementations in which an address of a target storage location is transferred using two bus packets, the address decoder 712 can decode the address information from two corresponding bus packets to form an address useable for accessing the target storage location of the memory chips 602a-d (FIGS. 6 and 7).

The data store status monitor 730 of the illustrated example determines the status of the memory chips 602a-d (block 922) (FIG. 9B). For example, the data store status monitor 730 determines whether the memory chips 602a-d are currently performing a read operation, a write operation, a self-refresh operation, a pre-charge operation, a power down operation or are currently in a sleep mode, a standby mode, or other low-power mode. If the memory chips 602a-d are performing any of these operations (or any other operations), the memory chips 602a-d are busy and cannot immediately perform the requested operation decoded at block 918. Otherwise, if the memory chips 602a-d are idle (i.e., not performing any operations that indicate they are busy), the memory chips 602a-d are not busy and can immediately perform the requested operation decoded at block 918.

The data store access arbiter 728 of the illustrated example determines whether the memory chips 602a-d are busy (block 924), for example, based on the status of the memory chips 602a-d determined at block 922. If the memory chips 602a-d are busy (block 924), the data store access arbiter 728 determines whether the memory operation queue 729 of the memory module 600 is too full to add another queued memory access request (block 926). For example, the data store access arbiter 728 may determine that the memory operation queue 729 is too full if the quantity of queued requests exceeds a threshold indicative of when no further memory access requests can be added to the queue 729. In some examples, the data store access arbiter 728 can determine whether it can service the requested memory access operation based on the number of access requests in the queue 729 without relying on a busy status of the memory chips 602a-d determined at block 924 based on the status of the memory chips 602a-d determined at block 922. Thus, in such some examples, the operations of blocks 922 and 924 may be omitted. If the memory operation queue 729 is too full (block 926), the data store access arbiter 728 of the illustrated example prompts or causes the message output subsystem 732 to respond to the bus packet received at block 902 with a negative acknowledgement (block 928) via, for example, a bus packet communication including an identification of the requesting device. In the illustrated example, the negative acknowledgement indicates that the memory access request cannot be granted (or cannot be serviced). In some examples, the negative acknowledgement causes the requesting device to re-send the memory access request to the memory module 600 at some later time (e.g., a time that may or may not be indicated by the data store access arbiter 728 or the module controller 614). In some examples, the negative acknowledgement can explicitly indicate that the requesting device should re-send the memory access request to the memory module 600 at some later time.

If at block 926, the data store access arbiter 728 determines that the memory operation queue 729 is not too full, control advances to block 930, at which the data store access arbiter 728 places the requested memory access operation in the memory operation queue 729 (block 930). The data store access arbiter 728 then determines whether the requested operation has been reached in the memory operation queue 729 for servicing (block 932). If the requested operation has not been reached in the memory operation queue 729, the data store access arbiter 728 continues to monitor the queue 729 at block 932 to determine when the requested operation is reached in the memory operation queue 729 for servicing.

When the requested operation is reached in the memory operation queue 729 for servicing (block 932), or if the data store access arbiter 728 determines that the memory chips 602a-d are not busy (block 924), the data store access arbiter 728 of the illustrated example causes the requested read or write operation(s) to be performed (block 934). As discussed above in connection with FIG. 7 and in connection with blocks 926, 930, and 932, the data store access arbiter 728 can queue the memory access operation if other memory access requests are still being performed or if other maintenance operations are being performed on the memory chips 602a-d such that the memory chips 602a-d cannot immediately be accessed to perform another memory access operation. Thus, the operation of block 934 can be an immediate or a delayed performance of the read or write operation(s) as determined by the data store access arbiter 728.

After the memory access operation is performed, the destination selector 734 selects a device identification (block 936) to identify the requesting memory controller (e.g., the memory controller 102) for which a response bus packet (e.g., the response bus packet 400 of FIG. 4) is to be communicated. The message generator 736 (FIG. 7) generates the response bus packet (block 938) including the device identification. If the requested memory access operation were a read request, the response bus packet can include the data retrieved from the memory chips 602a-d in a data field (e.g., the data field 406 of FIG. 4) and the message generator 736 can also store a corresponding checksum in a checksum field (e.g., the checksum field 408 of FIG. 4). If the requested memory access operation were a write request, the response bus packet can include an acknowledgement message acknowledging a successful write. The acknowledgement message could be included in a header field (e.g., the header field 402 of FIG. 4). The message output subsystem 732 communicates the response bus packet on the memory bus 106 (block 940).

After communicating the response bus packet (block 940) or after ignoring the received bus packet (block 910) (FIG. 9A) or after processing the hint information (block 916) (FIG. 9A), the example process of FIGS. 9A and 9B is ended.

Figure 10:
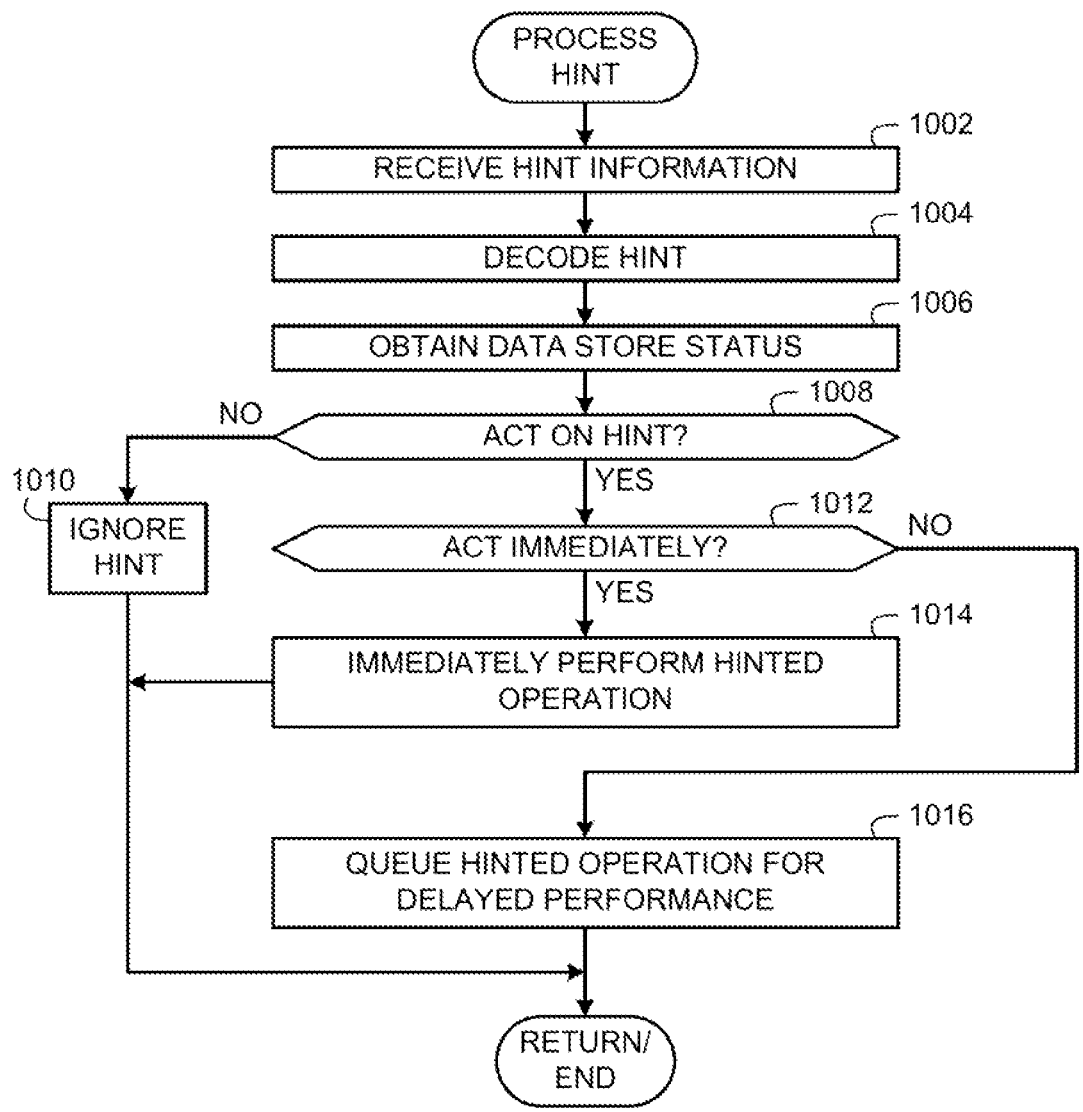
FIG. 10 depicts a flow diagram of an example process that can be implemented in memory modules to process received hint information.

FIG. 10 depicts a flow diagram of an example process that can be implemented in memory modules to process received hint information. The example process is described in connection with the memory module 600 of FIGS. 6 and 7, but may alternatively be implemented using other memories (e.g., the memory devices 502, 504, and 506 of FIG. 5 and/or the memory module 1200 of FIG. 12) and/or other types of memories. In addition, although FIG. 10 is described below in connection with the flow diagram as depicted, some examples may employ different operations in addition to or instead of the operations of FIG. 10. For instance, some operations of FIG. 10 may be omitted or combined with other operations or performed in a different order or in parallel with other operations.

Initially, the hint logic subsystem 716 (FIG. 7) receives the hint information (block 1002) from, for example, the message input subsystem 704 (FIG. 7). The hint decoder 718 (FIG. 7) decodes the hint information (block 1004). The hint controller 720 (FIG. 7) obtains the data store status (block 1006) of the memory chips 602a-d (FIGS. 6 and 7) from the data store status monitor 730 (FIG. 7). In this manner, the hint logic subsystem 716 can determine whether the memory module 600 can act on the hint. For example, if the memory chips 602a-d are busy with memory access requests (or maintenance operations) or if the data store access arbiter 728 (FIG. 7) has a queue of other memory access requests (from the same or different memory controllers) waiting to be performed, the hint controller 720 can determine that the memory module 600 cannot perform the hinted operation. In some instances, the hint controller 720 may determine that it can queue a hinted operation if the status of the memory chips 602a-d indicates that they are currently busy (e.g., with a memory access or maintenance operation) but that the operation will be finished soon and there are no other memory access requests queued by the data store access arbiter 728.

If the hint controller 720 determines that the memory module 600 cannot act on the hint (block 1008), the hint logic subsystem 716 ignores the hint (block 1010). Otherwise, if the hint controller 720 determines that the memory module 600 can act on the hint (block 1008), the hint controller 720 determines whether the memory module 600 can act immediately (block 1012). If the memory module 600 can act immediately on the hint (block 1012), the memory module 600 immediately performs the hinted operation (block 1014). For example, the hint controller 720 can instruct the maintenance controller 722 to perform the hinted operation. If the memory module 600 cannot act immediately on the hint (block 1012), the hint controller 720 queues the hinted operation (e.g., in the memory operation queue 729 of FIG. 7) for performing the hinted operation at a subsequent time (block 1016). After the hinted operation is queued (block 1016) or after the hinted operation is performed (block 1014) or if the hint is ignored (block 1010), control returns to a calling process or function such as the example process of FIGS. 9A and 9B, and the example process of FIG. 10 is ended.

Figure 11:
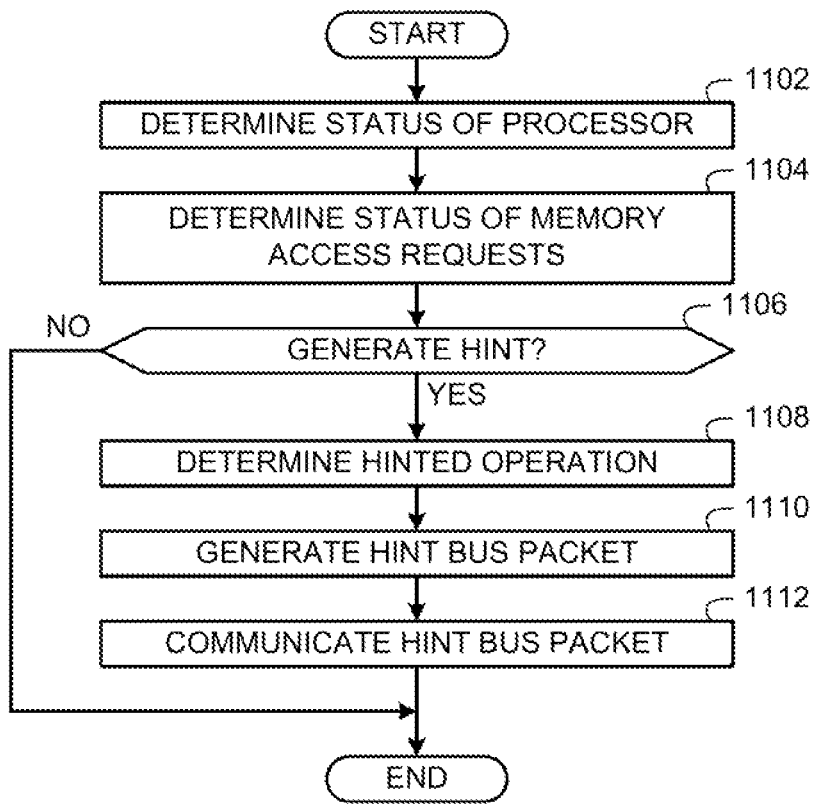
FIG. 11 depicts a flow diagram of an example process that can be implemented in a memory controller to generate hint information.

FIG. 11 depicts a flow diagram of an example process that can be implemented in a memory controller to generate hint information. The example process of FIG. 11 is described in connection with the memory controller 102 of FIGS. 1, 5, and 8, but may alternatively be implemented using other memory controllers or devices that access memory devices on memory buses such as the memory bus 106 of FIGS. 1, 5, 7, and 8. In addition, although FIG. 11 is described below in connection with the flow diagram as depicted, some examples employ different operations in addition to or instead of the operations of FIG. 11. For instance, some operations of FIG. 11 may be omitted or combined with other operations or performed in a different order or in parallel with other operations without departing from the scope and spirit of this application.

Initially, the hint generator 806 (FIG. 8) determines the status of a connected processor (e.g., the processor 116 of FIG. 1) (block 1102) to identify whether the processor is in an active state, an idle state, or in a low-power mode (e.g., sleep, deep-sleep, powered down, etc.). The hint generator 806 also determines the status of memory access requests (block 1104) received from the connected processor to identify whether any memory access requests are currently being processed or still need to be processed.

The hint generator 806 determines whether to generate a hint (block 1106). For example, the hint generator 806 can determine that a hint can be generated if the processor is in an idle or low-power mode or if there are no pending memory access requests from the processor. If the hint generator 806 determines that it can generate a hint (block 1106), the hint generator 806 determines hinted operation to generate (block 1108). For example, if the processor is in an idle or low-power mode, the hinted operation may inform one or more memory devices that they can enter a low-power mode. Or, if there are no pending requests but the processor is active, the hinted operation can be a self-refresh operation. In some instances, the hint may indicate a duration for an idle time of the memory controller 102 (e.g., a duration for which no memory access requests will be made by the memory controller 102), and the one or more memory devices can use the indicated idle time duration to determine which internal operation(s) it can perform during the idle time duration.

The message generator 812 (FIG. 8) generates a hint bus packet (block 1110) (e.g., the hint bus packet 300 of FIG. 3). If the hint is to be communicated to a single memory device (e.g., the DRAM memory 104), the device selector 814 (FIG. 8) can select the memory device identifier of the single memory device, and the message generator 812 can store the memory device identifier and the hinted operation in the hint bus packet. If the hint is a general hint applicable to all memory devices on the memory bus 106, a memory device identifier can be omitted from the hint bus packet and the hint bus packet can be communicated as a general broadcast bus packet.

The message output subsystem 808 communicates the hint bus packet on the memory bus 106 (block 1112). After the hint bus packet is communicated (block 1112) or if no hint is to be generated (block 1106), the example process of FIG. 11 is ended.

In some example implementations, one or more of the example processes of FIGS. 9A, 9B, 10, and/or 11 may be implemented using machine readable instructions that, when executed, cause a device (e.g., a programmable controller or other programmable machine or integrated circuit) to perform the operations shown in FIGS. 9A, 9B, 10, and/or 11. For instance, the example processes of FIGS. 9A, 9B, 10, and/or 11 may be performed using a processor, a controller, and/or any other suitable processing device. For example, the example processes of FIGS. 9A, 9B, 10, and/or 11 may be implemented in coded instructions stored on a tangible machine readable medium such as a flash memory, a read-only memory (ROM), and/or a random-access memory (RAM) associated with a processor or controller. As used herein, the term tangible computer readable medium is expressly defined to include any type of computer readable storage and to exclude propagating signals. Additionally or alternatively, the example processes of FIGS. 9A, 9B, 10, and/or 11 may be implemented using coded instructions (e.g., computer readable instructions) stored on a non-transitory computer readable medium such as a flash memory, a read-only memory (ROM), a random-access memory (RAM), a cache, or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals.

Alternatively, the example processes of FIGS. 9A, 9B, 10, and/or 11 may be implemented using any combination(s) of application specific integrated circuit(s) (ASIC(s)), programmable logic device(s) (PLD(s)), field programmable logic device(s) (FPLD(s)), discrete logic, hardware, firmware, etc. Also, the example processes of FIGS. 9A, 9B, 10, and/or 11 may be implemented as any combination(s) of any of the foregoing techniques, for example, any combination of firmware, software, discrete logic, and/or hardware. Further, although the example processes of FIGS. 9A, 9B, 10, and/or 11 are described with reference to the flow diagrams of FIGS. 9A, 9B, 10, and/or 11, other methods of implementing the processes of FIGS. 9A, 9B, 10, and/or 11 may be employed. For example, the order of execution of the blocks may be changed, and/or some of the blocks described may be changed, eliminated, sub-divided, or combined. Additionally, any or all of the example processes of FIGS. 9A, 9B, 10, and/or 11 may be performed sequentially and/or in parallel by, for example, separate processing threads, processors, devices, discrete logic, circuits, etc.

Although certain methods, apparatus, and articles of manufacture have been described herein, the scope of coverage of this patent is not limited thereto. To the contrary, this patent covers all methods, apparatus, and articles of manufacture fairly falling within the scope of the appended claims either literally or under the doctrine of equivalents.

What is claimed is:

1. A memory module, comprising:
   an interface to receive a request to access a memory of a memory module;
   a data store status monitor to determine a status of the memory;
   a message output subsystem to, when the memory is busy, respond to the request with a negative acknowledgement indicating that the request to access the memory is not grantable; and
   a data store access arbiter to, when the memory is busy, determine whether the request can be placed in a queue of the memory, the negative acknowledgment by the message output system being performed when the request cannot be placed in the queue.

2. A memory module as defined in claim 1, wherein the request cannot be placed in the queue when the queue is filled.

3. A memory module as defined in claim 1, wherein the request is received and the negative acknowledgement is sent using packet data communications.

4. A memory module as defined in claim 1, wherein the request to access the memory is a request to write data to the memory.

5. A memory module as defined in claim 4, wherein the memory is a first memory and the request is received from a second memory to write data to the first memory using a memory-to-memory transfer.

6. A memory module, comprising:
   an interface to receive a request to access a memory of a memory module;
   a data store status monitor to determine a status of the memory;
   a message output subsystem to, when the memory is busy, respond to the request with a negative acknowledgement indicating that the request to access the memory is not grantable; and
   a data store access arbiter to enable immediately servicing the request when the memory is not busy.

7. A memory module as defined in claim 6, wherein the request is received and the negative acknowledgement is sent using packet data communications.

8. A memory module as defined in claim 6, wherein the request to access the memory is a request to write data to the memory.

9. A memory module as defined in claim 8, wherein the memory is a first memory and the request is received from a second memory to write data to the first memory using a memory-to-memory transfer.

10. A method comprising:
    receiving a request to access a memory of a memory module;
    determining a status of the memory via a status monitor circuit of the memory module;
    when the memory is busy, responding to the request with a negative acknowledgement indicating that the request to access the memory is not grantable; and
    when the memory is busy, determining via a data store access arbiter circuit whether the request can be placed in a queue of the memory, the negative acknowledgment by the message output system being performed when the request cannot be placed in the queue.

11. A method as defined in claim 10, wherein the request cannot be placed in the queue when the queue is filled.

12. A method as defined in claim 10, wherein the request is received and the negative acknowledgement is sent using packet data communications.

13. A method as defined in claim 10, wherein the request to access the memory is a request to write data to the memory.

14. A method as defined in claim 13, wherein the memory is a first memory and the request is received from a second memory to write data to the first memory using a memory-to-memory transfer.

15. A method comprising:
    receiving a request to access a memory of a memory module;
    determining a status of the memory via a status monitor circuit of the memory module;
    when the memory is busy, responding to the request with a negative acknowledgement indicating that the request to access the memory is not grantable; and
    enabling via a data store access arbiter circuit immediate servicing of the request when the memory is not busy.

16. A method as defined in claim 15, wherein the request is received and the negative acknowledgement is sent using packet data communications.

17. A method as defined in claim 15, wherein the request to access the memory is a request to write data to the memory.

18. A method as defined in claim 17, wherein the memory is a first memory and the request is received from a second memory to write data to the first memory using a memory-to-memory transfer.

* * * * *